US012746151B2

(12) United States Patent
Heinzle

(10) Patent No.: US 12,746,151 B2
(45) Date of Patent: Sep. 29, 2026

(54) FLUID DISPENSER AND METHOD FOR MANUFACTURING A FLUID DISPENSER

(71) Applicant: Aptar Radolfzell GmbH, Radolfzell (DE)

(72) Inventor: Volker Heinzle, Krauchenwies (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 273 days.

(21) Appl. No.: 18/464,640

(22) Filed: Sep. 11, 2023

(65) Prior Publication Data

US 2024/0091057 A1 Mar. 21, 2024

(30) Foreign Application Priority Data

Sep. 16, 2022 (EP) .................................... 22196193

(51) Int. Cl.
*A61F 9/00* (2006.01)
*B05B 9/04* (2006.01)

(52) U.S. Cl.
CPC .............. *A61F 9/0008* (2013.01); *B05B 9/04* (2013.01)

(58) Field of Classification Search
CPC ..... B05B 9/04; B05B 11/0067; B65D 47/283; A61F 9/0008
See application file for complete search history.

(56) References Cited

U.S. PATENT DOCUMENTS 2,577,321 A 12/1951 Filger
3,945,381 A 3/1976 Silver
4,471,890 A 9/1984 Dougherty
4,553,686 A 11/1985 Dougherty
5,076,474 A 12/1991 Hansen
5,611,788 A 3/1997 Marchment
D852,351 S 6/2019 Alvino et al.
10,538,369 B2 * 1/2020 Ritsche .................. B65D 47/18
10,829,276 B2 * 11/2020 Höhm ................ B65D 47/2075
2003/0146245 A1 8/2003 Weiler et al.
(Continued)

FOREIGN PATENT DOCUMENTS

AU 634137 B3 2/1993
EP 0093493 A1 11/1983
WO WO8400707 A * 3/1984

OTHER PUBLICATIONS

European Search Report issued in corresponding European Application No. 22 19 6193.1 with English translation of categories of cited documents, dated Mar. 14, 2023 (6 pages).

*Primary Examiner* — Jennifer C Chiang
(74) *Attorney, Agent, or Firm* — FLYNN THIEL, P.C.

(57) ABSTRACT

Method for manufacturing a fluid dispenser. In a finished state, the fluid dispenser has a fluid store and a delivery opening through which fluid is discharged to the environment in a delivery direction. The fluid dispenser has a housing component through which the delivery opening is made and which has a delivery structure forming the delivery opening and/or adjoining the delivery opening, for influencing a delivery characteristic. This housing component having the delivery opening is manufactured firstly by manufacturing a base body by plastic injection moulding in a casting mold and then, in a region of a provisional delivery structure of the base body, a mechanical force is applied to deform the provisional delivery structure and hence create a definitive delivery structure.

16 Claims, 5 Drawing Sheets

(56) References Cited

U.S. PATENT DOCUMENTS

| | | | | |
|---|---|---|---|---|
| 2006/0258977 | A1 | 11/2006 | Lee | |
| 2007/0113841 | A1 | 5/2007 | Fuchs | |
| 2013/0075431 | A1 | 3/2013 | Wochele | |
| 2014/0020789 | A1 | 1/2014 | Duquet et al. | |
| 2016/0015887 | A1 | 1/2016 | Pananen et al. | |
| 2016/0236834 | A1 | 8/2016 | Erlhöfer | |
| 2017/0182249 | A1 | 6/2017 | Lee et al. | |
| 2019/0366376 | A1 | 12/2019 | Rossignol | |
| 2020/0078572 | A1 | 3/2020 | Kreutzmann et al. | |
| 2021/0283334 | A1 | 9/2021 | Lefebvre et al. | |
| 2021/0354152 | A1 | 11/2021 | Kreutzmann et al. | |
| 2022/0105524 | A1 | 4/2022 | Greiner-Perth | |
| 2025/0162769 | A1* | 5/2025 | Ciezarek ................ | B65D 47/18 |

* cited by examiner

FLUID DISPENSER AND METHOD FOR MANUFACTURING A FLUID DISPENSER

CROSS-REFERENCE TO RELATED APPLICATION

This claims priority from European Application No. 22196193.1, filed Sep. 16, 2022, the disclosure of which is hereby incorporated by reference in its entirety.

TECHNICAL FIELD

The invention concerns a method for manufacturing a fluid dispenser, and a fluid dispenser which can be manufactured in particular by means of this method.

BACKGROUND AND SUMMARY

Such a fluid dispenser, which can be manufactured by means of the method according to the invention, is normally used for delivering pharmaceutical or also cosmetic fluids. It has a fluid store for storing the fluid before delivery, and a delivery opening through which the fluid can be discharged to the environment in a delivery direction.

The suitable design of the delivery opening, and the delivery structure surrounding the delivery opening and in particular situated downstream thereof, depends on the nature of the dispenser and in particular also on the desired application form.

Typically, a fluid dispenser is manufactured—at least for some or most components—by means of plastic injection moulding. This means that plastic is introduced in liquid form into a cavity formed by a normally two-piece casting mould, where it cools and hardens, and the casting mould is then opened so that the resulting plastic component can be removed. Unless particular measures are taken, such as the use of so-called slides, this type of manufacture is associated with the requirement that, on opening the casting mould, the resulting plastic component remains removable from the mould, i.e. has no undercuts which hinder or prevent its separation from one of the casting mould halves forming the cavity. This requirement means that the components of the fluid dispenser, and in particular also those of the plastic component through which the delivery opening is made, are limited in their design, and in particular a design with a shape which not only tapers starting from the separating plane of the casting mould halves but also widens in places, can only be implemented with difficulty.

In the case of a fluid dispenser, this limits the design possibilities of said delivery structure in the region of the delivery opening.

One object of the invention is to provide a manufacturing method concerning a fluid dispenser, and a fluid dispenser which can be manufactured using this method, wherein with respect to design in the region of the delivery opening, the manufacturing method offers great flexibility at low cost.

To this end, a method is proposed for manufacturing a fluid dispenser with a fluid store and a delivery opening through which fluid can be discharged to the environment in a delivery direction.

In concrete terms, the invention here in one aspect concerns the manufacture of a housing component penetrated by a delivery opening and having a delivery structure forming the delivery opening and/or closely surrounding the delivery opening, for influencing a delivery characteristic of the delivery opening. The housing component may be an external housing component which, as well as the delivery opening, also has coupling means such as an internal thread or a latching edge for coupling to a fluid dispenser. The housing component may however also be a smaller housing component which is connected to other housing components to form an external surface of a delivery head.

The delivery structure of the housing component surrounds the discharge path and in particular influences the delivery characteristic by its design downstream of the narrowest cross-section of the discharge path. In particular, for the purpose of droplet formation, the delivery structure may be designed such that emerging fluid adheres to the delivery structure until it detaches in the form of a single droplet under the force of gravity.

According to one aspect of the invention, it is proposed that the housing penetrated by the delivery opening is manufactured in that firstly, in a first step, a base body is manufactured by plastic injection moulding in a casting mould. Here, preferably, a casting mould is used which has two casting mould halves forming a cavity, i.e. having no slides or similar for manufacturing a more complex design. The use of slides is however also possible with the method according to the invention. Preferably however, it does not then take place in the region of the delivery structure.

In particular, the base body of the housing component, i.e. the housing component in an intermediate state after first forming by plastic injection moulding, has a design in which the component, starting from a separating border of the two casting mould halves, tapers in both directions and has no widenings forming undercuts which could hinder the removal from the casting mould.

After completion of the plastic injection moulding, in a second step, a mechanical force is applied to the still unfinished delivery structure, which leads to a deformation of the base body and hence to formation of the delivery structure with its definitive design.

According to another aspect of the invention, it is therefore provided that the housing component with delivery opening is initially manufactured conventionally via an injection moulding process, and then a plastic deformation of the delivery structure takes place in order thereby to influence the delivery characteristic through the delivery opening.

The resulting housing component is usually combined with further components, in particular with a component forming the fluid store and further components of a delivery head, e.g. valve or pump components, which in the context of the invention however have no essential significance. In particular, the delivery head, which is provided with the delivery opening in the housing component manufactured according to the invention, may comprise an additional external housing which in particular has an opening at an end face, into which the housing component formed as the fluid discharge part is inserted.

The method according to one aspect of the invention offers two main advantages:

Firstly, housing components with an end widening and resulting undercut can be manufactured without the need for a particularly complex casting mould, for example with separately movable slides.

Secondly, different delivery structures can be created without the need for separate casting moulds. Instead, a uniform casting mould is used for two different designs of delivery structures, and after manufacture of the base body by injection moulding, starting from base bodies of identical structure to this point, by different force application to the originally identical delivery structures, differently formed delivery structures can be created which have different delivery characteristics. Accordingly, in particular it is proposed to manufacture housing components with different delivery structures starting from identical base bodies.

It is preferred that the mechanical force is applied by means of a die which, after the initial manufacture, presses on the delivery structure. In particular, it may be a metallic die which is part of the production system and acts automatically on the delivery structure with defined force/travel parameters during the manufacturing process. Preferably, the mechanical force may be applied by a die which is advanced to the base body in the main extent direction of the delivery opening, and there presses on the delivery structure from the inside or in particular from the outside, in particular is pressed onto the base body opposite the later outlet direction of the fluid.

The die, or another element for the purpose of force application according to the invention, may in particular have a widening shape so that, during its approach to the delivery structure, it comes into contact therewith and widens this increasingly during the continued advance. The shape of the delivery structure of the base body, before the deformation taking place in the second step, preferably already has an internal conical form or an internal cylindrical form, which is then widened in the second step, in particular by means of said widening die or other force application element.

Preferably, it is provided that at a distal end of the delivery structure, the widening taking place in the second step widens the cross-section of a clear internal diameter by at least 10%, preferably by at least 20%.

The objective of force application is a permanent change in the delivery structure, i.e. a plastic deformation of the plastic material. To achieve this, the force is preferably applied by means of a heated component. Depending on plastic used, the temperature of the component during deformation preferably lies at least at the Vicat softening temperature. For most plastic materials, this temperature is between 60° C. and 160° C. The method is in principle applicable to all plastics conventionally used for fluid dispensers.

The force application with the heated component can be achieved in particular if the force is applied to the delivery structure by means of the die when the base component is still warm after injection moulding. Alternatively or additionally, it may be provided that the force is applied directly with a heated die. In particular, to this end the die may be fitted with a heating element.

As well as using residual heat from the injection moulding and use of a heated die, it is naturally also possible to heat the base component as a whole in a separate heating step after injection moulding, in order then to apply the force in heated state.

The heating of the delivery structure during force application, in particular the use of a heated die for the purpose of force application, also offers the advantage that burrs remaining in the region of the delivery opening from the injection moulding can thereby be reduced or eliminated. In particular in manufacture of an eye-drop dispenser, this is a substantial advantage.

The force application to the delivery structure and the associated deformation need not necessarily take place by means of a separate tool such as said die, but may also use an element of the fluid dispenser itself. In particular, it may be provided that the mechanical force application and associated deformation take place using a protective cap of the fluid dispenser. For this, the protective cap has on its inside a widening structure tapering from the outside in the direction of the delivery opening, which is adapted to the provisional shape of the outlet structure of the base body after the first moulding such that this delivery structure is widened in the manner of a cup.

Such a procedure facilitates the method, since the second step—deformation of the delivery structure—is associated with the step of mounting the cap. Preferably, the protective cap is a second component separate from the housing component, which in particular is preferably manufactured separately. After the first moulding of the housing component with the delivery structure, and possibly assembly of this housing component with other housing components such as e.g. a fluid store or valve pump components, the protective cap is then fitted. During fitting of the protective cap, force is applied to the delivery structure and in particular it is radially widened. In particular, preferably the delivery structure is heated at this time in order to achieve the desired plastic deformation of the delivery structure by means of the protective cap and the widening structure provided thereon. By using the protective cap as the element influencing the delivery structure, also identical dispensers can therefore be provided with different delivery structures by means of different protective caps.

As well as said manufacturing method, the invention also concerns a fluid dispenser which in particular can be manufactured using this method. In particular, preferably this is a droplet dispenser for delivering separate individual droplets. Such a droplet dispenser has a delivery structure which, in the region of the delivery opening, has a droplet formation surface on which the discharged fluid settles. Only when the fluid quantity of a droplet has been reached does this droplet detach from the delivery structure under force of gravity.

A fluid dispenser according to the invention has a fluid store and a delivery opening through which the fluid can be discharged to the environment in a delivery direction. This delivery opening is preferably provided on a delivery head which is configured for coupling to a fluid dispenser. The fluid dispenser may in particular be configured as a pump dispenser or squeeze bottle dispenser. When configured as a pump dispenser, the dispenser has a pump device with a pump chamber which is provided with a valve on the input side and on the output side, and which can be operated by means of a control device, in particular by means of a knob provided on the side of a housing of the delivery head, in order to deliver fluid from the pump chamber and draw in fresh fluid from the fluid store. In the case of a squeeze bottle dispenser, no pump device is provided. Instead, the pressure is applied in that the fluid dispenser as a whole is elastically compressed and the fluid thereby pushed through to the delivery opening. Both in the case of a pump dispenser and also in the case of a squeeze bottle dispenser, it is preferably provided that a delivery valve is connected directly upstream of the delivery opening, which opens under positive pressure and thus allows discharge.

The fluid dispenser has a housing component, in particular an external housing of a delivery head or a fluid discharge part inserted therein, through which the delivery opening passes and which has a delivery structure forming the delivery opening and/or adjoining the delivery opening. This delivery structure, which in particular forms the above-mentioned droplet formation surface and may be provided downstream of the discharge opening, serves to influence the discharge characteristic. Said droplet formation is an example of this. The delivery structure could however also have a different design, for example to produce a fluid jet.

The feature of the fluid dispenser according to one aspect of the invention is that the delivery structure has on its outside a circumferential depression. In comparison with a cross-section of the delivery structure at a downstream distal end, the cross-section of the delivery structure in the region of the circumferential depression reduces in the manner of a constriction. In the case of a droplet dispenser, the distal end is formed preferably with an outer diameter of at least of at least 1 mm and/or at most 3 mm, preferably an outer diameter of at least 1.5 mm and/or at most 2.5 mm. In the region of the circumferential depression below this, the outer diameter preferably at least 10% smaller, preferably at least 20% smaller.

The size of the diameter at the distal end in particular for the purpose of droplet discharge depends on the desired droplet volume, taking into account the fluid and its viscosity and density, and the properties of the material of the delivery structure. The diameter should be selected such that a droplet of the desired volume can form here and, on reaching this volume, reliably detach under force of gravity from the delivery structure and the cup shape preferably provided here. The method according to one aspect of the invention allows, starting from base components of identical form after injection moulding, by subsequent deformation and in particular widening of the distal end of the delivery structure, the manufacture of delivery structures each with a design ideally adapted to the respective fluid.

The cup shape, which results from the circumferential depression below the distal end of the delivery structure, leads to advantageous geometric conditions at the upper end of the cup for preventing the escape of fluid from the inside of the delivery structure during droplet formation. On the outside of the delivery structure, this preferably has an external widening region widening continuously in the delivery direction, which extends from the circumferential depression up to the distal end of the delivery structure. An angle between a surface of the external widening region, i.e. a straight line lying in the plane of the widening region, and the discharge direction is preferably more than 20°, in particular preferably more than 30° or 40°.

Preferably, the flat or internally conical droplet formation surface formed by the delivery structure is delimited on the outside at the distal end of the delivery structure by a tear-off edge which hinders an escape of fluid. In particular, the tear-off edge may be formed with a curvature radius of more than 0.05 mm, in particular more than 0.1 mm, in order to avoid injury from the tear-off edge.

Preferably, the delivery structure has no burrs in the region of the depression. A burr in the region of the delivery structure should be avoided since this constitutes a danger in the case of medicaments applied to the eyes. If a sharp-edged burr comes into contact with the eye, it can cause injury.

The absence of burrs in the region of the depression can be achieved in particular by the above-described method. During shaping of a delivery structure with circumferential depression using previously conventional methods, this could only be achieved if the separating line of the casting mould halves is provided in the region of the depression, or if a casting mould with slides is used; however, the method according to the invention allows the circumferential depression to be produced by means of the two-stage method described, i.e. in a first injection moulding step, the base form is produced without depression, and this is then formed by subsequent widening of the delivery structure above the depression.

The delivery structure preferably has a cup-like widening in the respective widening regions on the outside and inside. Preferably, an angle between the surface of the external widening region and the discharge direction is smaller than an angle between a surface of the internal widening region and the discharge direction. The cup-like wall of the delivery structure is preferably thinner towards the distal end.

As already described above, it is possible to use the manufacturing method such that the plastic deformation of the delivery structure starting from the base form takes place using the protective cap as a force application element.

A fluid dispenser therefore preferably has a removable and refittable protective cap which covers the delivery opening when fitted, and on its inside has a widening structure which lies on an inside of the delivery structure when the protective cap is fitted. Because the design of the delivery structure is determined during manufacturing by means of the widening structure, the widening structure and the inside of the delivery structure lie particularly close together when the protective cap is fitted. This also constitutes an advantage in that, in later operation, this can very reliably displace fluid residue from the delivery structure when the protective cap is refitted to the fluid dispenser after use.

It may be advantageous if the housing component through which the delivery opening is made, and the protective cap or at least its widening structure, consist of different plastic materials. In particular, the widening structure may be made of a harder material and/or a material with higher softening temperature.

The deformation of the delivery structure, which is intended to take place on initial application of the protective cap or on use of the die, is at least partially plastic so that a residual deformation occurs. It may however also be provided—and achieved by suitable method parameters, in particular a suitably selected temperature—that the deformation is partially elastic so that when the protective cap is fitted, the delivery structure is under elastic tension.

The protective cap is preferably not simply a push-on cap but counters removal by form fit. This may be achieved in particular by a latching edge on the protective cap or by the design of the protective cap with a thread for coupling to an external housing of the delivery head.

The delivery opening and the delivery structure of the fluid dispenser usually have a rotationally symmetrical design. This is not however compulsory. It may also be advantageous to provide a non-rotationally symmetrical form, for example a polygonal cross-section or a cross-section with circumferential discrete bulges. In the case of a droplet dispenser, this may influence the separating tendency of a droplet.

BRIEF DESCRIPTION OF THE DRAWINGS

Further advantages and aspects of the invention arise from the claims and the following description of preferred exemplary embodiments of the invention which are explained below with reference to the figures.

DETAILED DESCRIPTION

Figure 1:
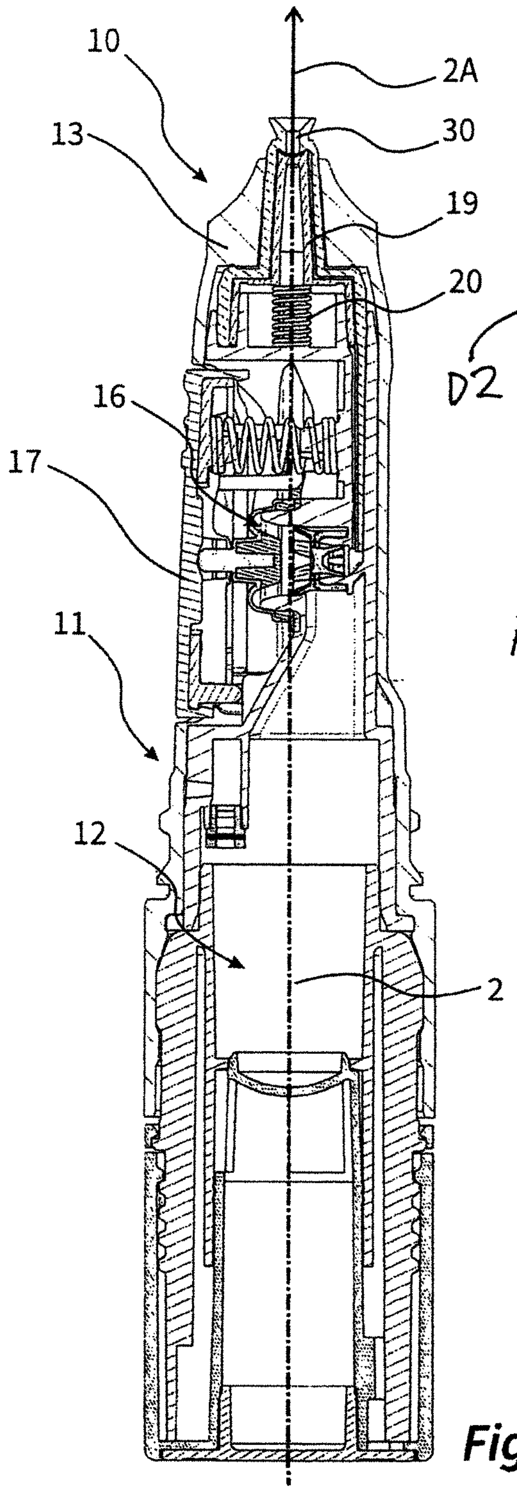
FIG. 1 shows a fluid dispenser according to the invention in a sectional illustration.
Figure 2:
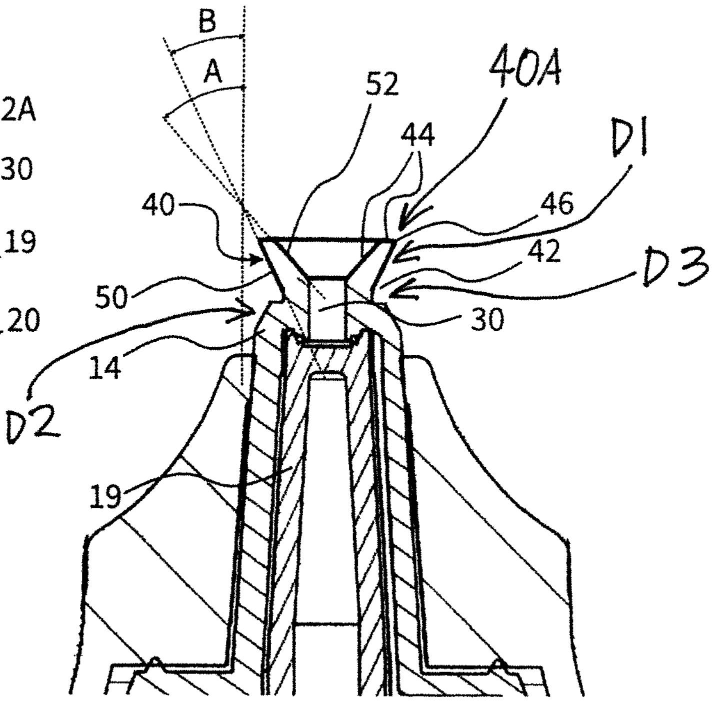
FIG. 2 shows the region of the delivery opening of the fluid dispenser in an enlarged view.

FIG. 1 shows a fluid dispenser 10 extending linearly in the direction of a main extent axis 2, in the present case for example a droplet dispenser. The fluid dispenser 10 has a delivery head 11 to which a fluid store 12 is coupled by means of a latch connection. Within the delivery head 11, a pump device 16 is provided which can be actuated via an actuation button 17 provided on the side of anthe outer housing 13 of the delivery head 11, and which, when actuated, draws in fluid from the fluid store 12 and conveys it in the direction of the delivery opening 30. FIG. 2 shows the region of the delivery opening 30 in an enlarged illustration.

The delivery opening 30 is part of a fluid discharge part 14. This is attached to an inner component 18 of the dispenser 10 and delimits the fluid path to the delivery opening 30. It has a sleeve-like portion which penetrates through an opening in the outer housing 13, and at the end of which a delivery structure 40 with a terminal distal end 40A is provided, as explained in more detail below.

Inside the fluid discharge part 14, a valve body 19 is provided which is pressed by a coil spring 20 in the direction of the delivery opening 30 and closes the delivery opening 30 in a closed state. Only when the fluid pressure in the region between the pump device 16 and the delivery opening 30 has reached a sufficient pressure level does the outlet valve open by displacement of the valve body 19 against the spring force of the coil spring 20, and fluid can emerge.

FIG. 2 clearly shows the delivery structure 40 in the region of the delivery opening 30. The delivery structure 40 means the geometry of regions of the fluid discharge part 14 which surround or adjoin the delivery opening 30 and influence the form of the discharge.

In the present case, the delivery structure 40 is designed for discharging droplets. The delivery structure is rotationally symmetrical to the main extent axis 2 and has a substantially cup-like design, which is delimited primarily by an internal widening region 52 widening in the direction of the delivery direction 2A, and an external widening region 50 also widening in the direction of the delivery direction 2A.

On the outside of the delivery structure 40, a circumferential depression 42 is provided. This is a type of constriction from which the fluid discharge part 14 widens in both directions. The delivery structure 40 has a first external diameter D1, a second external diameter D2 and a third external diameter D3 at the circumferential depression 42 axially between the first and second external diameters D1 and D2.

Figure 3:
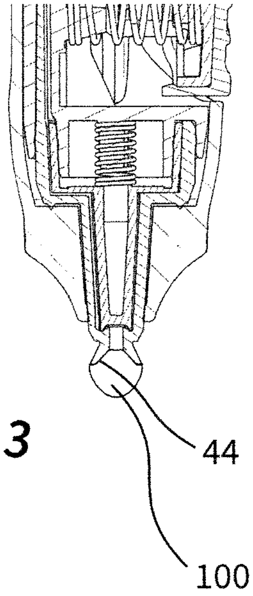
FIGS. 3 and 4 show the use of the fluid dispenser in various orientations.

As FIG. 3 illustrates, the inner widening region 52 forms a droplet formation surface 44. Fluid discharged through the delivery opening 30 is initially deposited in the area of this widening region 52, until the resulting droplet has reached a mass which separates it from the delivery structure 40 under the force of gravity. The widening region 52 and the end face of the delivery structure 40 together form a droplet formation surface 44.

The circumferential depression 42 allows provision of the illustrated angle B on the outside of the distal end of the fluid discharge part 14. This angle B, which is preferably smaller than the angle A between the main extent axis 2 and the inner widening region 52, is advantageous for preventing the fluid from not only collecting in the widening region 52 and on the end face, but also from passing around the distal outer edge into the external widening region 50. This guarantees that the fluid quantity of a droplet 100 does not deviate from the intended fluid quantity.

Figure 4:
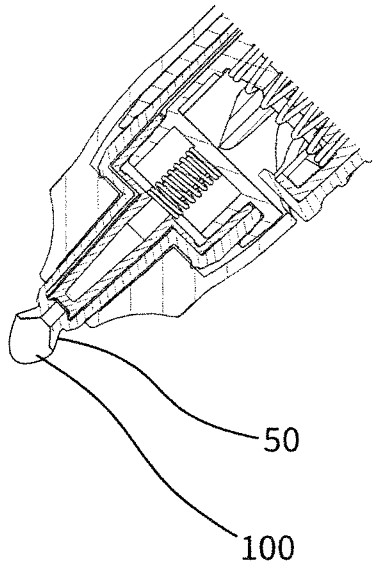

FIG. 4 illustrates that the angle A plays a greater role if the droplet dispenser is held obliquely during droplet discharge. If this is the case, the tendency of the fluid to pass from the inner droplet formation surface 44 to the outer widening region 50 is increased. The greater the angle A, the less critical such an oblique orientation is with respect to achieving a uniform droplet volume.

The described design of the delivery structure 40 cannot simply be achieved by plastic injection moulding.

FIGS. 5A to 5G show a possible sequence for manufacturing of the fluid discharge part 14.

Figure 5A:
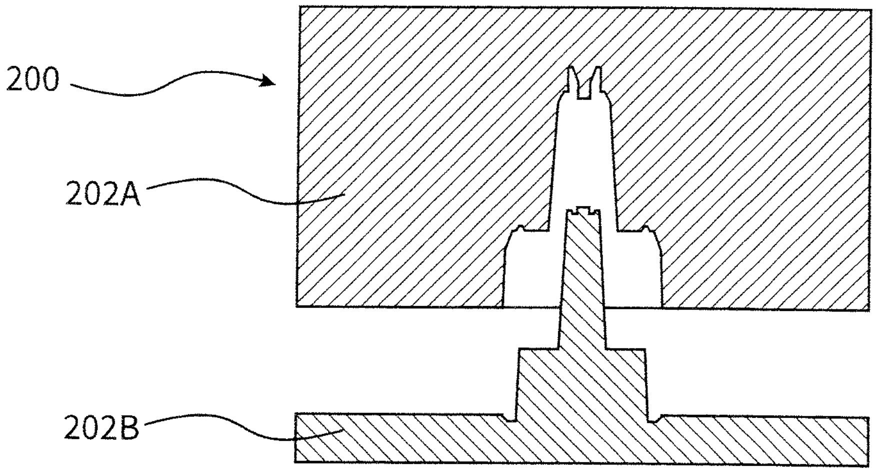
FIGS. 5A to 5F show a method for manufacturing a fluid discharge part 14 of the dispenser 10.
Figure 5B:
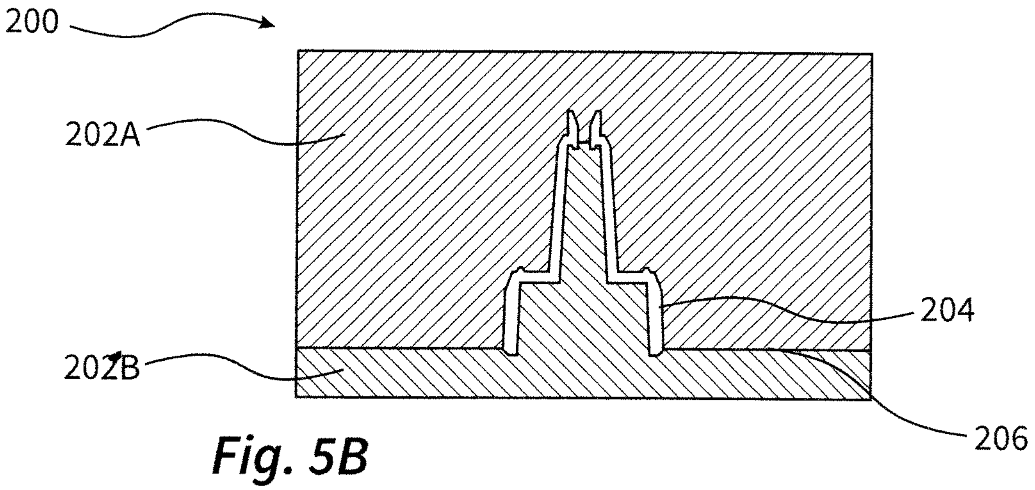
Figure 5C:
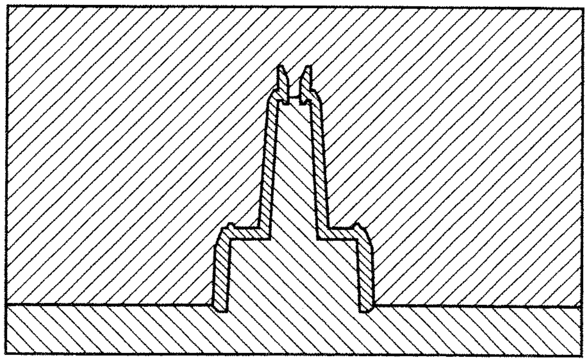

Firstly, a base body 14' is manufactured. This is achieved by plastic injection moulding. A casting tool 200 with two casting mould halves 202A and 202B is used, as shown in FIG. 5A. In the closed state in FIG. 5B, the two casting mould halves 202A, 202B form a cavity 204 which has the negative form of the base body 14'. Liquid plastic is injected into this cavity 204, as shown in FIG. 5C.

After hardening of the plastic, the casting tool 200 is opened and the base body 14' can be removed. As evident from FIG. 5A, the two casting mould halves 202A, 202B are formed such that there are no undercuts which could hinder removal of the base body 14' from the mould. This can therefore be removed without deformation.

Figure 5D:
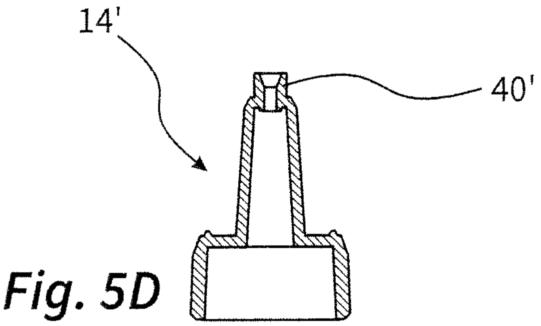

FIG. 5D shows the base body 14' after injection moulding. Since the separating boundary 206 lies on the far side of the delivery structure 40', which is still provisional in the state of FIG. 5D, this is free from burrs.

Figure 5E:
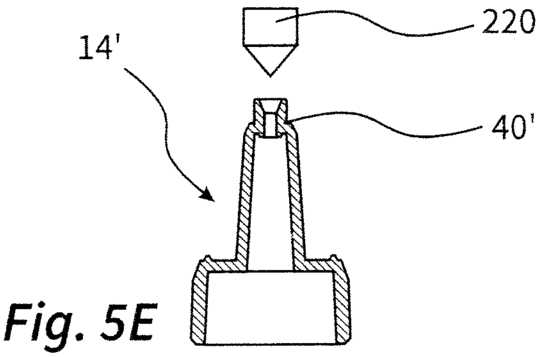

Starting from the state of FIG. 5D, a second step in manufacturing of the fluid discharge part 14 takes place. A die 220 with a conical tip is now advanced from the outside in the direction of the main extent axis 2, as illustrated in FIG. 5E.

Figure 5F:
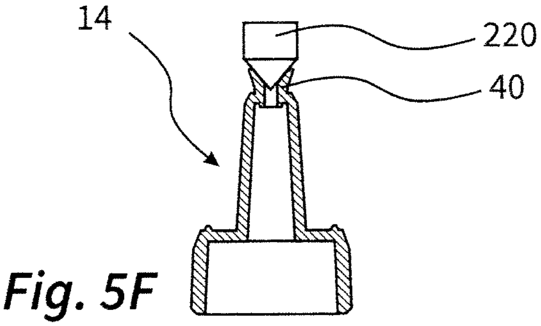

As shown in FIG. 5F, this die 220 presses the provisional delivery structure 40' outward and thus deforms this plastically. In particular, at this time the base body 14' may be heated, either because of the preceding injection moulding step or because of a separate heating. Thus the tendency of the delivery structure 40 to deform plastically can be increased. In addition or alternatively to a prior heating of the base body 14', it is also conceivable to heat the die 220 itself.

The temperature to be selected here depends on the plastic used. Preferably, the temperature lies above the softening temperature of the respective plastic. In the case of polypropylene, this temperature is for example around 150° C.

Figure 5G:
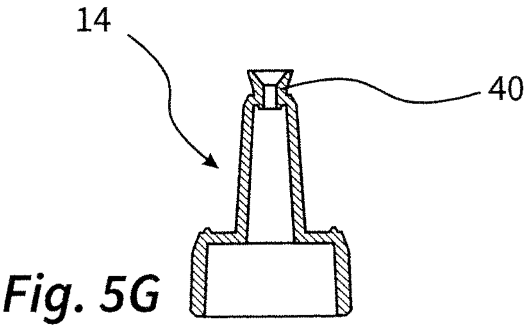
FIG. 5G shows the die removed.

As soon as plastic deformation has taken place, the die 220 may be removed again as shown in FIG. 5G. This leaves the now complete fluid discharge part 14, the delivery structure 40 of which has the shape already illustrated in FIG. 2. The cup-like widening allows a particularly precise dosing since the discharged droplets differ only very slightly in their fluid volume.

Figure 6:
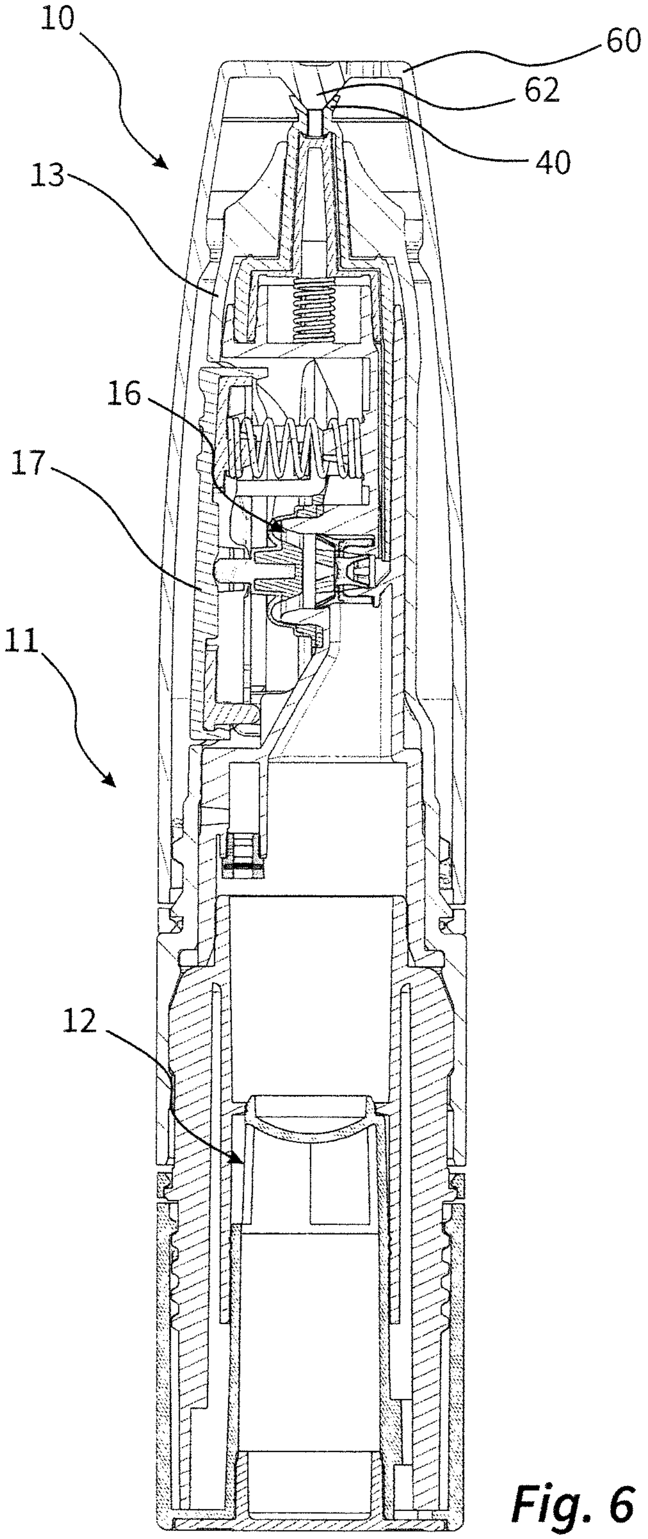
FIG. 6 shows a fluid dispenser which is manufactured by means of a partially alternative method.

FIG. 6 shows an alternative design. The distinguishing feature here is that the fluid discharge part 14 is initially left in the shape of the base body 14', and the plastic deformation is caused by a protective cap 60.

To this end, the protective cap 60 on its inside has a widening structure 62. Preferably, the protective cap as a whole, or at least the widening structure 62, is made of a harder material or a material with higher softening temperature than the material of the fluid discharge part 14.

When the protective cap 60 is fitted to the dispenser for the first time, preferably screwed on by means of a thread, this widening structure 62—like the die 220 in the case of FIGS. 5A to 5F—presses the delivery structure 40 outward and causes a plastic deformation. Preferably, this shaping takes place under the influence of heat. In particular, the fluid discharge part 14 may be at least partially heated when the protective cap 60 is fitted.

The invention claimed is:

1. A fluid dispenser, the fluid dispenser comprising:
- a fluid store;
- a delivery opening through which fluid is discharged to the environment in a delivery direction; and
- a housing component penetrated by the delivery opening and having a delivery structure adjoining the delivery opening and surrounding a discharge path, for influencing a delivery characteristic, the delivery structure having an outside and including a circumferential depression and an external widening region both on the outside thereof, the external widening region widening continuously in the delivery direction, and an angle between a surface of the external widening region and the delivery direction is more than 20°.

2. The fluid dispenser according to claim 1, wherein the delivery structure has on an inside an internal widening region, the internal widening region widening in the delivery direction.

3. A fluid dispenser, the fluid dispenser comprising:
- a fluid store;
- a delivery opening through which fluid is discharged to the environment in a delivery direction; and
- a housing component penetrated by the delivery opening and having a delivery structure adjoining the delivery opening and surrounding a discharge path, for influencing a delivery characteristic, the delivery structure having an outside and an inside, the delivery structure including a circumferential depression and an external widening region both on the outside, the external widening region widening continuously in the delivery direction, the delivery structure including an internal widening region on the inside, the internal widening region widening in the delivery direction,
- wherein an angle between a surface of the external widening region and the delivery direction is smaller than an angle between a surface of the internal widening region and the delivery direction.

4. A fluid dispenser, the fluid dispenser comprising:
- a fluid store;
- a delivery opening through which fluid is discharged to the environment in a delivery direction; and
- a housing component penetrated by the delivery opening and having a delivery structure adjoining the delivery opening and surrounding a discharge path, for influencing a delivery characteristic, the delivery structure having a circumferential depression on an outside thereof, the delivery structure having a terminal distal end, a first external diameter oriented transverse to a central axis of the delivery opening and spaced a first distance from the terminal distal end, a second external diameter transverse to the central axis of the delivery opening and spaced a second distance from the terminal distal end, the second distance being greater than the first distance, the delivery structure at the circumferential depression having a third external diameter transverse to the central axis of the delivery opening, the third external diameter at the circumferential depression being disposed axially between the first and second external diameters and the first and second external diameters both being greater than the third external diameter.

5. A fluid dispenser, the fluid dispenser comprising:
- a fluid store;
- a delivery opening through which fluid is discharged to the environment in a delivery direction; and
- a housing component penetrated by the delivery opening and having a delivery structure adjoining the delivery opening and surrounding a discharge path, for influencing a delivery characteristic, the delivery structure having a circumferential depression on an outside thereof, the delivery structure defining a terminal distal end, the circumferential depression being disposed upstream, with respect to the delivery direction, of the terminal distal end, wherein starting from the circumferential depression, the delivery structure widens externally in diameter in both an upstream direction and in a downstream direction.

6. The fluid dispenser according to claim 5, wherein:
- the fluid dispenser is configured as a droplet dispenser; and
- the delivery structure comprises a droplet formation surface on which droplet formation surface fluid discharged through the discharge opening adheres to form a droplet until the droplet detaches under force of gravity.

7. The fluid dispenser according to claim 6, wherein the droplet formation surface is delimited on an outside by a tear-off edge, wherein the tear-off edge is formed with a curvature radius of more than 0.05 mm.

8. The fluid dispenser according to claim 6, wherein the droplet formation surface has an outer diameter of at least 1 mm and/or at most 3 mm.

9. The fluid dispenser according to claim 5, wherein:
- the fluid dispenser has a removable and refittable protective cap covering the delivery opening when fitted; and
- the protective cap has an inwardly pointing widening structure lying against an inside of the delivery structure when the protective cap is fitted.

10. The fluid dispenser according to claim 9, wherein the protective cap is formed as a screw cap and/or the delivery structure is held under elastic tension by the widening structure when the protective cap is fitted.

11. The fluid dispenser according to claim 5, wherein the delivery opening and/or the delivery structure has a shape deviating from rotational symmetry.

12. The fluid dispenser according to claim 5 wherein:
- the fluid dispenser is configured as a pump dispenser and has a manually actuatable pump device with a pump chamber and with an inlet valve and an outlet valve; or
- the fluid dispenser is configured as a squeeze bottle dispenser and has as a fluid dispenser a squeeze bottle compressible manually for delivery purposes.

13. The fluid dispenser according to claim 5, wherein:
- the fluid store is filled with a pharmaceutical fluid; and/or
- the fluid store has an internal volume of less than 200 ml.

14. A fluid dispenser comprising:
- a fluid store; and
- a delivery head including a housing attached to the fluid store, the housing comprising a fluid discharge housing part defining a delivery opening for discharging fluid to an environment of the fluid dispenser in a delivery direction, the delivery opening defining a central axis, the fluid discharge housing part including a delivery structure surrounding the delivery opening and configured for influencing a delivery characteristic of fluid discharged from the delivery opening, the delivery structure defining a terminal distal end of the delivery head and having an external annular surface surrounding the central axis of the delivery opening, the delivery structure having a first external diameter oriented transverse to the central axis of the delivery opening and spaced a first distance from the terminal distal end, a second external diameter transverse to the central axis of the delivery opening and spaced a second distance from the terminal distal end, the second distance being greater than the first distance, the delivery structure including a depression extending circumferentially along the annular external surface and having a third external diameter transverse to the central axis of the delivery opening, the third external diameter at the depression being disposed axially between the first and second external diameters and the first and second external diameters both being greater than the third external diameter.

15. The fluid dispenser according to claim 14, wherein the delivery structure includes oppositely-facing inner and outer annular surfaces facing away from one another, the outer annular surface forming part of the external annular surface of the delivery structure, the inner annular surface having an internal diameter and the outer annular surface having an external diameter, the internal and external diameters of the respective inner and outer annular surfaces both increasing in the delivery direction.

16. The fluid dispenser according to claim 15, wherein the terminal distal end of the delivery structure includes an end face, and the inner annular surface and the end face together define a droplet formation surface disposed at the terminal distal end of the delivery structure.

* * * * *